United States Patent [19]

Innocenti et al.

[11] 4,294,833
[45] Oct. 13, 1981

[54] SUBSTITUTED 4-HYDROXY-ISOPHTHALIC ACID PICOLYLAMIDES HAVING A PHARMACEUTICAL ACTIVITY IN THROMBOEMBOLIC DISORDERS

[75] Inventors: Franco Innocenti; Giovanni Orzalesi; Ivo Volpato, all of Florence, Italy

[73] Assignee: Societa Italo-Britannica, Florence, Italy

[21] Appl. No.: 937,732

[22] Filed: Aug. 29, 1978

[30] Foreign Application Priority Data

Sep. 6, 1977 [IT] Italy ................... 50896 A/77

[51] Int. Cl.³ ............... A61K 31/44; C07D 213/40
[52] U.S. Cl. ................... 424/263; 424/266; 546/265; 546/267
[58] Field of Search ............ 260/295.5 A, 295 AM; 424/266, 263; 546/267, 265

[56] References Cited

U.S. PATENT DOCUMENTS 3,923,820 12/1975 Roldan et al. .............. 260/295 AM
3,973,026 8/1976 Orzalesi et al. .................. 424/263

Primary Examiner—Henry R. Jiles
Assistant Examiner—Robert C. Whittenbaugh
Attorney, Agent, or Firm—Cushman, Darby & Cushman

[57] ABSTRACT

There are prepared 4-hydroxy-isophthalic acid bis (3- or 4-picolyl-amides) of the formula (I)

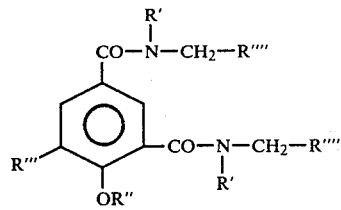

where R' is H or an aliphatic or alicyclic hydrocarbon group with 1 to 16 carbon atoms, R'''' is 3-pyridyl or 4-pyridyl, R''' is H, Cl, NO₂, or —OCH₃, R'' is an aliphatic or alicyclic hydrocarbon group with 1 to 8 carbon atoms with the exception that when R'''' is 3-pyridyl and R' and R''' are both H, then R'' is an aliphatic or alicyclic hydrocarbon radical with 3 to 8 carbon atoms. The compounds are useful in inhibition of blood platelet aggregation.

24 Claims, No Drawings

SUBSTITUTED 4-HYDROXY-ISOPHTHALIC ACID PICOLYLAMIDES HAVING A PHARMACEUTICAL ACTIVITY IN THROMBOEMBOLIC DISORDERS

The present invention relates to compounds of the class comprising substituted or not substituted isophtalic acid picolylamides having a pharmaceutical activity, which are able to inhibit the aggregation of blood platelets and to control blood thromboembolic disorders and to delay blood clotting. The invention relates also to a process for carrying out the synthesis of said new compounds as well as to their pharmaceutical applications.

The new chemical compounds which are the object of the present invention have the following general formula (I):

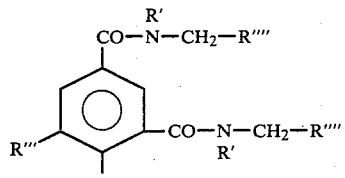

In formula (I), the nitrogen atom of the pyridine ring can be in 3-position or in 4-position, so that said compounds can be defined as substituted 4-hydroxy-isophthalic acid bis(3-picolylamides) or bis(4-picolylamides). In formula (I), $R'$ is H or an aliphatic or alicyclic hydrocarbon radical with 1 to 6 carbon atoms, $R''''$ is 3-pyridyl or -4-pyridyl $R'''$ is H, Cl, $NO_2$ or $OCH_3$, $R''$ is H or an aliphatic or alicyclic hydrocarbon radical having 1 to 8 carbon atoms, with the exception that when the nitrogen atom N in the pyridine rings is in 3-position and $R'$ and $R'''$ are both H, then $R''$ is an aliphatic or alicyclic hydrocarbon radical with 3 to 8 carbon atoms.

By the term aliphatic hydrocarbon radical is meant a straight or cross-linked chain, saturated or unsaturated aliphatic hydrocarbon radical and by the term alicyclic hydrocarbon radical is meant those saturated or unsaturated radicals which also can be substituted by aliphatic groups.

It has been known that the members of the above class of compounds in which the pyridine N is in 3-position, $R'$ is H, $R'''$ is H and $R'$ is H, methyl or ethyl, particularly N,N'-bis(3-picolyl)-4-methoxyisophthalanide, have an anticoagulant, fibrinolytic and platelet antiaggregant activity (see U.S. Pat. No. 3973 026 issued Aug. 3, 1976 and Italian Pat. No. 1016 005 filed July 1, 1970, granted May 30, 1977, an abridgment of which was published in Chem. Abstr. Vol. 75/71, 110153H).

It has now been surprisingly discovered that many other compounds of the same class show such an anticoagulant, fibrinolytic and platelet antiaggregant activity, so as to provide drugs having a high therapeutical index.

Said activity could not be foreseen a priori, because it could not be expected that by variously changing the functional substituents which appear in the compound structure, particularly the chain length of the substituent $R''$, the pharmaceutical activity would be maintained without the occurrence of intolerance effects.

Therefore a new class of compounds has been discovered having a high therapeutical index, namely a high ratio of activity to toxicity, which offer to those skilled in the art a wide spectrum of active agents useful in medicine to control thromboembolic disorders with a wide range of drug and dosage selection for specific cases.

According to the present invention, the compounds corresponding to the above defined formula can be obtained by reacting the dichloride of the selected acid (namely 4-hydroxy-isophthalic acid substituted as above indicated) with a selected amine (namely a primary or secondary 3-picolylamine or 4-picolylamine), in the presence of a proton acceptor which, depending on the particular case, can be pyridine or triethylamine (method A).

Alternatively, the above defined compounds can be obtained by directly condensing the substituted 4-hydroxy-isophthalic acid and the selected picolylamine in the presence of DCC (dicyclohexylcarbodiimide, $C_6H_{11}N=C=NC_6H_{11}$) or phosphorus trichloride as dehydratant.

For the sake of clarity and not in a limitative sense, in the following some possible embodiments of the invention are described.

In the following "acid" means a substituted 4-hydroxy-isophthalic acid and picolylamine means a 3-or 4-picolylamine as above specified.

Method $A_1$

Acid dichloride: 0.01 moles
Picolylamine: 0.03 moles
Triethylamine: 0.03 moles

In a 150 ml, three neck flask, provided with reflux condenser, valved funnel and mechanical stirrer, there were charged 50 ml THF (tetrahydrofuran) and the above indicated amounts of picolylamine and triethylamine. This was reflux heated on an electric bath and the acid dichloride, dissolved in 50 ml THF, was added dropwise, said addition being carried out in about 4 hours. This was refluxed for about 20 hours and thereupon the solvent was evaporated under reduced pressure. The raw residue was taken up in chloroform (about 150 ml) and the chloroform solution was extracted twice by 0.5 normal NaOH and twice by $H_2O$. The washed organic phase was dried on anhydrous $MgSO_4$, filtered, and the solvent was evaporated under reduced pressure. The product obtained was crystallized in a suitable solvent (water, methanol, isopropanol, isopropyl ether, ethyl acetate, and the like).

Method $A_2$

Acid dichloride: 0.01 moles
Picolylamine: 0.02 moles

In a 250 ml, three neck flask, equipped as described under Method $A_1$, there was charged the amine dissolved in 50 ml anhydrous pyridine. There was added acid dichloride dissolved in a minimum amount of THF under stirring at room temperature. The heat generated by the reaction was dispersed by continuous stirring until the mixture reached the room temperature. By diluting with $H_2O$ a precipitate was obtained which was recovered on a filter, washed, dried and crystallized in a suitable solvent, as described in the method $A_1$ above.

Method $B_1$ (direct condensation):

Acid: 0.01 moles
Picolylamine: 0.02 moles
DCC: 0.10 moles

In a 200 ml flask there were charged the above reactants dissolved in dioxane, the flask was plugged by a $CaCl_2$ controlled tube and the mixture was reacted at room temperature for 72 hours. At the end of the reaction, the mixture was concentrated under reduced pressure, by evaporating most of the solvent to obtain a residue which, taken up in $H_2O$ and alcalized by $NaCO_3$, provided a precipitate. The precipitate was collected on a filter, washed, dried and crystallized in a suitable solvent (water, methanol, isopropanol, isopropyl ether and the like).

Method $B_2$ (direct condensation):
Acid: 0.01 moles
Picolylamine: 0.02 moles
$PCl_3$: 0.03 moles In a 1000 ml flask the acid and amine were charged. They were additioned with 300 ml anhydrous benzene containing $PCl_3$ and the mixture was reflux heated for about 140 hours. At the end of the reaction, the precipitate was filtered and recovered in $H_2O$. This was alcalized by NaOH, filtered, and a precipitate was collected which, after washing and drying, was crystallized in a suitable solvent (water, methanol, benzene, isopropyl ether, ethyl acetate, and the like).

The new compounds so obtained, having a structure of bis(3-picolylamides) or bis(4-picolylamides) have been submitted to pharmacological screening in order to examine their activity, with particular consideration to those parameters which are concerned with the clinic field of thromboembolic disorders considered as a whole.

As a result of the pharmacological tests, it has been found that the products of the present invention have to be classified as drugs which act at the level of the blood coagulative system, in that they have a marked activity as platelet antiaggregant and antithrombin agents, associated with a relatively low acute toxicity. From the complex of the parameters ascertained, it follows that said compounds have a therapeutical utility in any pathological state characterized by modification of platelet aggregation, fibrinogenesis and blood coagulum.

Another object of the invention therefore are pharmaceutical compositions having particular activity as fibrinolytic, antithrombin and platelet antiaggregant drugs, characterized by including, as an active principle, a compound of the general formula (I) associated with a pharmaceutically compatible vehicle.

Pharmacological study

Determination of the platelet aggregation inhibitory activity in vivo

The activity of the above described compounds as platelet antiaggregant was tested in vivo on rabbits, by the Born aggregometer. The inhibition of the aggregation curve induced by ADP and thrombin was assessed with different drug concentrations according to the platelet reactivity. New Zealand rabbits which had been held fasting for 12 hours with water ad libitum, were anaesthetized with Nembutal in a dose of 35 mg/kg intramuscolarly. The blood was withdrawn from the carotidal arthery, before (control) and 2, 4, and 6 hours after the intraperitoneal injection of the compounds under examination (at the dose indicated below). The blood samples were taken up in a 3.8% aqueous solution of sodium citrate in a ratio 10:1 and thereupon centrifuged at 1500 r.p.m. for 10 minutes, for obtaining a PRP (platelet rich plasma). A portion of such a plasma was thereupon centrifuged at 8000 r.p.m. for 10 minutes, for obtaining a PPP (platelet lean plasma) which was used for zeroing the measuring apparatus.

From the results of said experiments, there was determined the dose of each product in mg/kg body weight able to induce a 50% inhibition of the aggregation curve ($DI_{50}$) after treatment, referred to the curve obtained by the same control plasma before treatment.

Determination of the antithrombin activity

The antithrombin activity on the PRP (platelet rich plasma) obtained following the above described method was assessed by Hartert's thromboelastograph (Hellige model). The coagulation was induced by adding to 0.25 ml of plasma 0.06 ml of a thrombin solution (Roche Topostasin ® per os) at 60 units*, pH 7.4**. The antithrombin activity was assessed in terms of a percent decrease of the index $(ma/[r+k])$ which was calculated from the thromboelastograph diagram, wherein r is the reaction time, k is the speed of the coagulum formation and ma is the maximum spread of the tong, after an intraperitoneal treatment with a dose of 20 mg/kg of each compound under examination, referred to the same index obtained before the treatment (control).

*=NIH/ml;
**=phosphate buffer.

Determination of the anticoagulant activity

The anticoagulant activity was also assessed on PRP of animals treated as described in the preceding methods, by using again Hartert's thromboelastograph method.

The plasma coagulation was induced by adding to 0.25 ml PRP a 1.29% solution of $CaCl_2$.

The anticoagulant effect was determined as a percent increase of the total time for the coagulum formation (the index $r+k$ can be obtained from the thromboelastograph diagram) in a plasma after treatment, referred to the same index obtained before the treatment (control). Again the dose level was 25 mg/kg for each compound under examination, intraperitoneally.

Determination of the fibrinolytic activity

The determination of the fibrinolytic activity was made following the Fearnley method for the lysis of the blood coagulum in toto.

0.2 ml of blood were withdrawn from the marginal vein of the ear of rabbits treated in the same way as the previously described tests, before and after an intraperitoneal injection of the compounds under test at a dose level of 25 mg/kg for each compound.

The blood samples were placed in test tubes containing 1.7 ml of phosphate buffer at pH 7.4 and 0.1 ml of thrombin (Roche Topostasin ® per os) at 50 units NIH/ml, and maintained in an ice bath. The test tubes were maintained at said temperature for 30 minutes and thereupon were transferred to a temperature controlled water bath at 37° C.

The fibrinolytic activity was determined as a percent decrease of the coagulum weight, measured after incubation for 30 minutes at 37° C.

Toxicological study

The acute toxicity limit was determined intraperitoneally on male Swiss mice, weighing 20±2 g, held fasting for 18 hours with water ad libitum.

The animals were maintained under observation for 7 days of treatment, by examining the general symptomatology and noting the death sequency. The preliminary $DL_{50}$ in mg/kg body weight was calculated by graphic interpolation of the results as obtained.

Results of the pharmacological determinations

The compounds according to the invention show clear effects as platelet antiaggregant, anticoagulant, fibrinolytic and antithrombin agents, said effects being surprisingly associated with a relatively low acute toxicity. Said compounds appear to be usefully employable in therapy for pathological states affected by platelet hyperaggregability, eccessive readiness to coagulation, insufficient fibrinolysis and increased thrombin activity.

The results obtained with the compounds having the above identified structure are reported in the following Tables, wherein there are indicated the substituents R', R" and R''' for the individual compounds.

In tables I and II are further indicated for each compound the method of preparation; the melting point PF in °C; the platelet antiaggregant activity (AAP) expressed in terms of $DI_{50}$ in mg/kg, referred to ADP and thrombin respectively; the antithrombin activity (AT) in %; the anticoagulant activity (AC) in %; the fibrinolytic activity (FL) in %; the acute toxicity ($LD_{50}$) in mice, intraperitoneally, in mg/kg, as previously defined.

In table I there are listed compounds in which the nitrogen atom of the pyridine ring is in 3-position, obtained from 3-picolylamine or a functional derivative thereof.

In table II there are listed compounds in which the nitrogen atom of the pyridine ring is in 4-position, obtained from 4-picolylamine or a functional derivative thereof.

The individual compounds, isolated and purified, have been analyzed by centesimal elementary analysis in the micro scale and the analytical results have confirmed their calculated formula within the standard limits allowed for said determinations.

Examples 1 to 16 and 22 show constant therapeutical values, while the substituent in R" varies; examples 17 to 21 show that when in R''' the H atom is replaced by a methoxy group, high therapeutical values are still obtained; examples 23 to 30 show that when H is replaced by Cl in R''', high therapeutical values are still obtained; examples 31 to 33 show that when the substituent H is maintained in R' and R", while the substituent in R''' is selected from —NO$_2$, Cl, —OCH$_3$, high therapeutical properties are maintained; examples 34 to 38 show different combinations of substituents for R" and R'''.

Examples 39 to 46 show various valid substituents for R'; examples 47 to 52 further show high therapeutical properties of the compounds when the substituent R''' is Cl and hydrocarbon groups having different chain lengths are selected for R' and R"; examples 53 to 56 show that good therapeutical properties are similarly obtained when R''' is H and R' and R" are hydrocarbon radicals with a high number of carbon atoms; and examples 57 to 71 which are concerned with 4-picolylamides, show that said compounds have high therapeutical properties when the indicated substituents are selected for R" (examples 57 to 65), R''' (examples 66 to 68) and R' (examples 69 to 71).

As will be appreciated from comparing compounds homogeneous to each other (for instance the compounds of examples 1-6), that although the acute toxicity increases with an increasing number of carbon atoms in the substituent R", also the therapeutical effects surprisingly increase with an increasing number of carbon atoms, so that the various compounds have a therapeutical index useful for medical applications.

From a consideration of the test results one can appreciate the utility of the new compounds according to the present invention. Said compounds are therefore particularly suitable for therapeutic use in the treatment, prevention and/or maintenance of cases of thromboembolic disorders, such as myocardial infarction, cerebrovascular disorders, peripheral venous thrombosis, coronary disease, acute pulmonary embolism, and the like, as well as for use in cardiosurgery.

Consequently, the compounds of the present invention show, in a marked and surprising manner, favorable effects in comparison with well known compounds used in the same field, in the totality of the functional parameters concerning the treatment of pathological state in thromboembolic disorders, associated with a sufficiently low toxicity.

Furthermore, said new compounds have a therapeutical index higher than that of other well known compounds, such as N,N'-bis(3-picolyl)-4-methoxy isophthalamide described in U.S. Pat. No. 3,973,026. That was not obvious to foresee, in view of the wide range of functional substituents appearing in the formula of the compounds of the invention, as it was neither obvious to foresee the lack of intolerability at the experimental dosage level.

The application conditions in which said results have been obtained allow to establish different routes of clinical administration for the compounds of the invention at different dose levels, which can be established for each individual case under treatment depending on the type of treatment the physician intends to carry out, namely a preventive, priming or maintenance treatment.

The drugs according to the invention can be supplied in clinical use for oral administration in the form of tablets, pills, granules, capsules, drops, syrup, and the like.

It can be supplied for rectal administration in the form of suppositories and for the parentheral administration in the form of injectable solutes, associated with well known pharmaceutically compatible vehicles.

The daily dosage of active principle administrable in clinical use through said routes of administration is preferably as follows:

(a) 1000 to 3000 mg/die orally;
(b) 100 to 1000 mg/die intramuscularly;
(c) 20 to 250 mg/die intravenously;
(d) 600 to 2500 mg/die, rectally.

Preferred amounts of active principle for a single oral dose are 500 mg and 1000 mg, associated with usual pharmacological excipients.

TABLE I

| Example No. | R' | R" | R''' | Preparation Method | Mt. Pt. (°C.) | $DI_{50}$ ADP | $DI_{50}$ Thrombin | AT (%) | AC (%) | FL (%) | $DL_{50}$ |
|---|---|---|---|---|---|---|---|---|---|---|---|
| 1 | H | —(CH$_2$)$_2$CH$_3$ | H | A$_1$ | 136–8 | 27,5 | 19,3 | 38,6 | 21,5 | 32,4 | 600 |
| 2 | H | —(CH$_2$)$_3$CH$_3$ | H | A$_1$ | 147–9 | 26,7 | 18,2 | 40,1 | 23,2 | 35,7 | 573 |
| 3 | H | —(CH$_3$)$_4$CH$_3$ | H | A$_1$ | 161–3 | 25,3 | 17,5 | 43,0 | 27,4 | 36,2 | 380 |
| 4 | H | —(CH$_2$)$_5$CH$_3$ | H | A$_2$ | 174–6 | 22,9 | 17,3 | 47,6 | 19,5 | 41,3 | 175 |
| 5 | H | —(CH$_2$)$_6$CH$_3$ | H | A$_2$ | 180–2 | 24,6 | 18,1 | 46,5 | 18,0 | 38,8 | 181 |
| 6 | H | —(CH$_2$)$_7$CH$_3$ | H | A$_2$ | 197–9 | 25,9 | 19,4 | 45,4 | 16,9 | 36,4 | 187 |
| 7 | H | —CH$_2$—CH=CH$_2$ | H | B$_1$ | 128–31 | 36,3 | 19,2 | 51,5 | 14,5 | 44,7 | 374 |
| 8 | H | —(CH$_2$)$_2$CH=CH$_2$ | H | B$_1$ | 140–2 | 35,5 | 25,7 | 50,6 | 14,2 | 42,1 | 362 |
| 9 | H | —(CH$_2$)$_3$CH=CH$_2$ | H | B$_1$ | 156–8 | 36,2 | 23,2 | 49,9 | 14,5 | 40,3 | 375 |

TABLE I-continued

| Example No. | R' | R'' | R''' | Preparation Method | Mt. Pt. (°C.) | DI₅₀ ADP | DI₅₀ Thrombin | AT (%) | AC (%) | FL (%) | DL₅₀ |
|---|---|---|---|---|---|---|---|---|---|---|---|
| 10 | H | —(CH₂)₄CH=CH₂ | H | B₁ | 163-5 | 29,4 | 21,1 | 52,6 | 12,6 | 43,9 | 194 |
| 11 | H | —CH₂CH=CHCH₃ | H | B₁ | 148-52 | 25,3 | 18,6 | 52,3 | 13,5 | 44,2 | 178 |
| 12 | H | —CH₃(CH₂)₂ | H | A₁ | 153-5 | 50,2 | 30,9 | 25,6 | 12,7 | 20,2 | 615 |
| 13 | H | —(CH₂)₂CH(CH₃)₂ | H | A₁ | 187-9 | 48,3 | 27,1 | 28,5 | 24,5 | 21,9 | 173 |
| 14 | H | —CH(CH₃)CH₂CH₃ | H | A₁ | 177-9 | 46,4 | 29,7 | 38,1 | 22,3 | 22,5 | 227 |
| 15 | H | —CH₂CH(CH₃)₂ | H | A₁ | 161-3 | 52,6 | 33,0 | 25,5 | 17,6 | 19,8 | 471 |
| 16 | H | —C(CH₃)₃ | H | A₁ | 158-9 | 45,2 | 30,3 | 27,6 | 13,6 | 21,9 | 325 |
| 17 | H | —CH₂CH=CH₂ | —OCH₃ | B₂ | 141-2 | 51,7 | 32,6 | 36,0 | 14,1 | 23,0 | 298 |
| 18 | H | —CH(CH₂)(CH₂) (cyclopropyl) | —OCH₃ | B₂ | 149-51 | 29,4 | 22,0 | 33,4 | 20,1 | 28,6 | 228 |
| 19 | H | —CH(CH₂)(CH₂)(CH₂) (cyclobutyl) | —OCH₃ | B₂ | 161-3 | 34,7 | 25,2 | 32,8 | 15,6 | 28,1 | 254 |
| 20 | H | Cyclopentyl | —OCH₃ | B₂ | 170-2 | 35,6 | 21,4 | 32,6 | 12,9 | 27,9 | 375 |
| 21 | H | Cyclohexyl | —OCH₃ | B₂ | 183-5 | 35,8 | 24,5 | 32,5 | 12,5 | 28,3 | 378 |
| 22 | H | —CH₂C≡CH | H | B₁ | 141-3 | 36,5 | 24,4 | 33,1 | 13,6 | 29,2 | 382 |
| 23 | H | —CH₃ | Cl | A₁ | 114-6 | 63,4 | 46,9 | 22,5 | 12,2 | 16,8 | 425 |
| 24 | H | —(CH₂)₄CH₃ | Cl | A₁ | 137-9 | 41,3 | 35,6 | 24,4 | 16,0 | 6,4 | 371 |
| 25 | H | —CH₂CH=CH₂ | Cl | A₁ | 138-40 | 59,5 | 35,4 | 40,6 | 15,5 | 25,9 | 184 |
| 26 | H | —(CH₂)₃CH₃ | Cl | A₁ | 125-7 | 43,7 | 30,2 | 33,5 | 22,2 | 28,4 | 205 |
| 27 | H | —(CH₂)₂CH(CH₃)₂ | Cl | A₁ | 153-5 | 40,0 | 27,9 | 35,1 | 23,8 | 28,8 | 195 |
| 28 | H | —CH₂C(CH₃)₃ | Cl | A₁ | 146-8 | 45,3 | 31,0 | 27,9 | 19,6 | 25,5 | 215 |
| 29 | H | —C(CH₃)₂CH₂CH₃ | Cl | A₁ | 160-2 | 44,1 | 30,7 | 27,3 | 20,0 | 24,1 | 206 |
| 30 | H | —CH(CH₂CH₃)₂ | Cl | A₁ | 158-60 | 42,2 | 29,5 | 27,9 | 22,3 | 25,8 | 198 |
| 31 | H | H | NO₂ | A₂ | 141-3 | 36,6 | 27,0 | 23,1 | 13,6 | 20,5 | 345 |
| 32 | H | H | Cl | A₁ | 130-2 | 50,2 | 33,6 | 22,2 | 11,8 | 17,3 | 425 |
| 33 | H | H | —OCH₃ | B₁ | 161-3 | 58,4 | 38,9 | 20,3 | 11,2 | 15,5 | 570 |
| 34 | H | —CH₂C(CH₃)₃ | H | A₁ | 186-8 | 35,6 | 27,3 | 29,7 | 13,6 | 22,7 | 351 |
| 35 | H | —CH₂C(CH₃)₃ | NO₂ | A₂ | 191-3 | 37,1 | 29,7 | 25,4 | 12,6 | 20,2 | 194 |
| 36 | H | —CH₂CH=CH₂ | NO₂ | A₂ | 192-5 | 36,3 | 27,1 | 23,0 | 11,9 | 19,1 | 267 |
| 37 | H | —CH₂C(CH₃)₃ | —OCH₃ | B₂ | 178-80 | 44,6 | 32,0 | 25,5 | 14,2 | 21,9 | 378 |
| 38 | H | —C(CH₃)₂CH₂CH₃ | Cl | A₁ | 158-60 | 54,3 | 34,6 | 22,0 | 12,9 | 19,3 | 322 |
| 39 | —CH₃ | —CH₃ | H | B₂ | 142-5 | 59,8 | 42,0 | 26,6 | 12,5 | 19,2 | 610 |
| 40 | —C₂H₅ | —CH₃ | H | B₁ | 150-2 | 60,2 | 42,3 | 28,9 | 13,4 | 20,6 | 605 |
| 41 | —(CH₂)₂CH₃ | —CH₃ | H | B₁ | 158-60 | 65,1 | 46,5 | 26,3 | 15,8 | 22,3 | 620 |
| 42 | —(CH₂)₃CH₃ | —CH₃ | H | A₁ | 163-4 | 66,4 | 47,2 | 28,7 | 14,5 | 21,7 | 623 |
| 43 | —CH(CH₃)₂ | —CH₃ | H | A₁ | 155-7 | 27,3 | 20,6 | 39,4 | 20,7 | 33,6 | 478 |
| 44 | —CH₂CH(CH₃)₂ | —C₂H₅ | H | A₁ | 178-80 | 28,7 | 20,9 | 38,6 | 19,3 | 32,5 | 465 |
| 45 | —(CH₂)₂CH(CH₃)₂ | —C₂H₅ | H | B₁ | 183-6 | 30,6 | 22,3 | 35,8 | 16,3 | 29,9 | 460 |
| 46 | —(CH₂)₃CH(CH₃)₂ | —C₂H₅ | H | B₁ | 188-90 | 34,3 | 24,7 | 32,7 | 15,5 | 29,1 | 451 |
| 47 | —C(CH₃)₂CH₂CH₃ | —CH=CHCH₃ | Cl | B₁ | 195-7 | 55,8 | 36,2 | 25,6 | 12,8 | 19,5 | 210 |
| 48 | —CH₂C(CH₃)₃ | —CH=CHCH₃ | Cl | B₁ | 186-8 | 50,3 | 31,9 | 27,6 | 14,4 | 20,1 | 207 |
| 49 | —(CH₂)₂CH(CH₃)₂ | —CH=CHCH₃ | Cl | B₁ | 190-2 | 49,0 | 30,2 | 27,9 | 15,3 | 21,7 | 193 |
| 50 | —CH(CH₂CH₃)₂ | —CH=CHCH₃ | Cl | B₁ | 188-91 | 52,2 | 33,8 | 27,6 | 13,8 | 24,6 | 198 |
| 51 | —(CH₂)₄CH₃ | —CH=CHCH₃ | Cl | B₁ | 171-4 | 51,6 | 32,4 | 28,2 | 15,7 | 26,1 | 205 |
| 52 | —CH₃ | —C(CH₃)=CH₂ | Cl | B₂ | 163-6 | 49,2 | 32,1 | 29,1 | 14,2 | 26,7 | 194 |
| 53 | —CH₃ | —CH₂CH=CHCH₃ | H | A₁ | 177-80 | 27,5 | 19,6 | 47,9 | 15,1 | 40,5 | 215 |
| 54 | H | —CH(CH₃)CH=CH₂ | H | A₁ | 160-3 | 32,3 | 21,2 | 46,3 | 18,7 | 35,2 | 355 |
| 55 | H | —CH=C(CH₃)₂ | H | A₁ | 173-5 | 28,2 | 20,5 | 32,5 | 19,2 | 29,5 | 338 |
| 56 | —CH(CH₃)₂ | —CH₂C(CH₃)=CH₂ | H | A₁ | 184-6 | 29,1 | 21,4 | 47,3 | 18,6 | 38,1 | 352 |

TABLE II

| Example No. | R' | R'' | R''' | Preparation Method | Mt. Pt. (°C.) | DI₅₀ ADP | DI₅₀ Thrombin | AT (%) | AC (%) | FL (%) | DL₅₀ |
|---|---|---|---|---|---|---|---|---|---|---|---|
| 57 | H | H | H | B₁ | 203-4 | 26,0 | 19,2 | 38,4 | 19,0 | 32,1 | 661 |
| 58 | H | —CH₃ | H | A₁ | 166-7 | 28,1 | 21,3 | 37,0 | 18,2 | 31,7 | 704 |
| 59 | H | —(CH₂)₂CH₃ | H | A₁ | 180-3 | 25,2 | 18,1 | 39,1 | 20,6 | 32,8 | 623 |
| 60 | H | —(CH₂)₅CH₃ | H | A₁ | 188-9 | 20,3 | 17,5 | 48,6 | 22,2 | 38,5 | 206 |
| 61 | H | —CH₂CH=CH₂ | H | B₁ | 171-4 | 28,6 | 19,5 | 52,8 | 15,6 | 45,0 | 392 |
| 62 | H | —CH(CH₃)₂ | H | A₁ | 176-8 | 46,8 | 32,3 | 26,5 | 12,0 | 21,7 | 618 |
| 63 | H | —(CH₂)₂CH(CH₃)₂ | H | A₁ | 185-7 | 42,9 | 28,4 | 29,2 | 22,6 | 23,2 | 185 |
| 64 | H | —CH(CH₃)CH=CH₂ | H | B₁ | 179-81 | 35,1 | 24,0 | 45,9 | 19,2 | 33,6 | 360 |
| 65 | H | —CH=C(CH₃)₂ | H | B₂ | 180-3 | 36,7 | 24,5 | 34,2 | 23,8 | 26,5 | 240 |
| 66 | H | —CH₃ | Cl | B₁ | 174-6 | 67,2 | 42,5 | 25,0 | 13,6 | 20,2 | 437 |
| 67 | H | —CH₂CH=CH₂ | Cl | B₁ | 183-5 | 55,6 | 34,2 | 39,8 | 14,6 | 27,1 | 187 |
| 68 | —CH₃ | —C(CH₃)=CH₂ | Cl | B₂ | 180-2 | 47,5 | 30,0 | 35,2 | 15,5 | 30,0 | 255 |
| 69 | —CH₃ | —CH₂CH=CHCH₃ | H | B₁ | 176-9 | 26,1 | 19,3 | 48,7 | 14,2 | 41,6 | 210 |
| 70 | —(CH₂)₂CH₃ | —CH₂C(CH₃)=CH₂ | H | A₁ | 198-9 | 30,6 | 20,8 | 48,2 | 18,9 | 39,3 | 360 |
| 71 | —CH(CH₃)₂ | —CH₃ | Cl | A₁ | 181-4 | 28,1 | 19,6 | 53,9 | 25,6 | 47,7 | 384 |

What is claimed is:

1. 4-hydroxy-isophthalic acid bis(3-or 4-picolylamides) of the formula I:

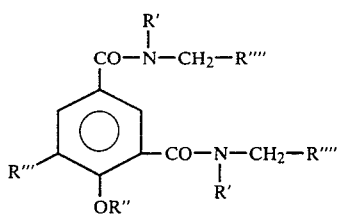

wherein R' is H or an aliphatic or alicyclic hydrocarbon group with 1 to 6 carbon atoms, R'''' is 3-pyridyl or 4-pyridyl, R''' is H, Cl, NO₂, or —OCH₃, R'' is an aliphatic or alicyclic hydrocarbon group with 1 to 8 carbon atoms, with the exception that when R'''' is 3-pyridyl and R' and R''' are both H, then R'' is an aliphatic or alicyclic hydrocarbon group with 3 to 8 carbon atoms.

2. A compound according to claim 1, wherein said alicyclic hydrocarbon groups are substituted by aliphatic hydrocarbon groups.

3. A compound of claim 1, wherein the N atom in the pyridine rings is in the 3-position, R' and R''' are H and R'' is —(CH₂)₂CH₃, —(CH₂)₃CH₃, —(CH₃)₄CH₃, —(CH₂)₅CH₃, —(CH₂)₆CH₃, —(CH₂)₇CH₃, —CH₂—CH═CH₂, —(CH₂)₂CH═CH₂, —(CH₂)₃CH═CH₂, —(CH₂)₄CH═CH₂, —CH₂CH═CHCH₃, —CH₃(CH₂)₂, —(CH₂)₂CH(CH₃)₂, —CH(CH₃)CH₂CH₃, —CH₂CH(CH₃)₂, —O(CH₃)₃, —CH₂C≡CH, —CH₂C(CH₃)₃, —CH(CH₃)CH═CH₂, or —CH═C(CH₃)₂.

4. A compound of claim 1, wherein the N atom in the pyridine rings is in the 3-position, R' is H, R''' is —OCH₃ and R'' is —CH₂CH═CH₂,

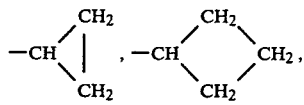

cyclopentyl, cyclohexyl, or —CH₂C(CH₃)₃.

5. A compound of claim 1, wherein the N atom in the pyridine rings is in the 3-position, R' is H, R''' is Cl and R'' is —CH₃, —(CH₂)₄CH₃, —CH₂CH═CH₂, —(CH₂)₃CH₃, —(CH₂)₂CH(CH₃)₂, —CH₂C(CH₃)₃, —C(CH₃)₂CH₂CH₃, —CH(CH₂CH₃)₂, or C(CH₃)₂CH₂CH₃.

6. A compound of claim 1, wherein the N atom in the pyridine rings is in the 3-position, R' and R'' are H, and R''' is NO₂, Cl or —OCH₃.

7. A compound of claim 1, wherein the N atom in the pyridine rings is in the 3-position, R' is H, R''' is NO₂ and R'' is —CH₂C(CH₃)₃ or —CH₂CH═CH₂.

8. A compound of claim 1, wherein the N atom in the pyridine rings is in the 3-position, R'' is —CH₃, R''' is H and R' is —CH₃, —C₂H₅, —(CH₂)₂CH₃, —(CH₂)₃CH₃, or —CH(CH₃)₂.

9. A compound of claim 1, wherein the N atom in the pyridine rings is in the 3-position, R'' is —C₂H₅, R''' is H and R' is —CH₂CH(CH₃)₂, —(CH₂)₂CH(CH₃)₂, or —(CH₂)₃CH(CH₃)₂.

10. A compound of claim 1, wherein the N atom is the pyridine rings is in the 3-position, R'' is —CH═CHCH₃, R''' is Cl and R' is —C(CH₃)₂CH₂CH₃, —CH₂C(CH₃)₃, —(CH₂)₂CH(CH₃)₂, —CH(CH₂CH₃)₂, or —(CH₂)₄CH₃.

11. A compound of claim 1, wherein the N atom in the pyridine rings is in the 3-position, R' is CH₃, R'' is —C(CH₃)═CH₂, and R''' is Cl.

12. A compound of claim 1, wherein the N atom in the pyridine rings is in the 3-position, R' is CH₃, R'' is —CH₂CH═CHCH₃, and R''' is H.

13. A compound of claim 1, wherein the N atom in the pyridine rings is in the 3-position, R' is —CH(CH₃)₂, R'' is —CH₂C(CH₃)═CH₂, and R''' is H.

14. A compound of claim 1, wherein the N atom in the pyridine rings is in the 4-position, R' and R''' are both H and R'' is H, —CH₃, —(CH₂)₂CH₃, —(CH₂)₅CH₃, —CH₂CH═CH₂, —CH(CH₃)₂, —(CH₂)₂CH(CH₃)₂, —CH(CH₃)CH═CH₂, or —CH═C(CH₃)₂.

15. A compound of claim 1, wherein the N atom in the pyridine rings is in the 4-position, R' is H, R''' is Cl and R'' is —CH₃ or —CH₂CH═CH₂.

16. A compounds of claim 1, wherein the N atom in the pyridine rings is in the 4-position, R' is —CH₃, R'' is -C(CH₃)═CH₂ and R''' is Cl.

17. A compound of claim 1, wherein the N atom in the pyridine rings is in the 4-position, R' is —CH₃, R'' is —CH₂CH═CHCH₃ and R''' is H.

18. A compound of claim 1, wherein the N atom in the pyridine rings is in the 4-position, R' is —(CH₂)₂CH₃, R'' is —CH₂C(CH₃)═CH₂ and R''' is H.

19. A compound of claim 1, wherein the N atom in the pyridine rings is in the 4-position, R' is —CH(CH₃)₂, R'' is —CH₃ and R''' is Cl.

20. A pharmaceutical composition for the inhibition of blood platelet aggregation containing, as an active principle, an effective amount of a compound of formula (I) of claim 1 and a pharmaceutically compatible vehicle.

21. A pharmaceutical composition effective as antithrombin drug containing, as an active principle, an effective amount of a compound of formula (I) of claim 1 and a pharmaceutically compatible vehicle.

22. A pharmaceutical composition effective as an anticoagulant drug containing, as an active principle, an effective amount of a compound of formula (I) of claim 1 and a pharmaceutically compatible vehicle.

23. A pharmaceutical composition effective as a fibrinolytic drug, containing, as an active principle, an effective amount of a compound of formula (I) of claim 1 and a pharmaceutically compatible vehicle.

24. A pharmaceutical composition effective for a combined action as platelet antiaggregant, antithrombin, anticoagulant and fibrinolytic drug, containing, as an active principle, an effective amount of a compound of formula (I) of claim 1 and a pharmaceutically compatible vehicle.

* * * * *